(12) United States Patent
Karuppiah et al.

(10) Patent No.: US 11,981,945 B2
(45) Date of Patent: May 14, 2024

(54) PROCESS OF PRODUCING MONOTERPENES

(71) Applicant: C3 Bio-Technologies Limited, Lancaster (GB)

(72) Inventors: Vijaykumar Karuppiah, Didcot (GB); Nicole G. H. Leferink, Manchester (GB); Nigel S. Scrutton, Cheshire (GB)

(73) Assignee: C3 BIOTECHNOLOGIES LIMITED, Lancaster (GB)

( * ) Notice: Subject to any disclaimer, the term of this patent is extended or adjusted under 35 U.S.C. 154(b) by 0 days.

(21) Appl. No.: 17/238,312

(22) Filed: Apr. 23, 2021

(65) Prior Publication Data

US 2021/0238640 A1    Aug. 5, 2021

Related U.S. Application Data

(62) Division of application No. 16/482,574, filed as application No. PCT/GB2018/050223 on Jan. 26, 2018, now abandoned.

(30) Foreign Application Priority Data

Jan. 31, 2017 (GB) ...................... 1701548

(51) Int. Cl.
C12P 17/06 (2006.01)
C12N 9/88 (2006.01)
C12P 7/04 (2006.01)

(52) U.S. Cl.
CPC ............... *C12P 17/06* (2013.01); *C12N 9/88* (2013.01); *C12P 7/04* (2013.01); *C12Y 402/03025* (2013.01); *C12Y 402/03026* (2013.01); *C12Y 402/03108* (2015.07)

(58) Field of Classification Search
CPC .. C12P 17/02; C12P 7/04; C12P 5/007; C12P 5/002; C12P 5/026; C12P 17/06; C12Y 402/03108; C12Y 402/03026; C12Y 402/03025; C12N 9/88
See application file for complete search history.

(56) References Cited

U.S. PATENT DOCUMENTS

2016/0068882 A1   3/2016   Zhang et al.
2018/0291403 A1  10/2018   Hoshino ................. C12P 5/007

FOREIGN PATENT DOCUMENTS

WO   2015189428 A1   12/2015
WO   2016008883 A1    1/2016

OTHER PUBLICATIONS

Leferink et al., Supporting information, A 'Plug and Play' Platform for the Production of Diverse Monoterpene Hydrocarbon Scaffolds in *Escherichia coli*. ChemsitrySelect, Copyright Wiley-VCH Verlag Gmbh & Co. KGaA, 69451 Weinheim, 2016, pp. 1-41 (Year: 2016).*
Mendez-Perez et al., Production of Jet Fuel Precursor Monoterpenoids From Engineered *Escherichia coli*. Biotechnology and Bioengineering, 2017, vol. 114(8): 1703-1712. (Year: 2017).*
Alonso-Gutierrez et al., Metabolic engineering of *Escherichia coli* for limonene and perillyl alcohol production. Metabol. Eng., 2013, vol. 19: 33-41. (Year: 2013).*
Tsuruta et al., High-Level Production of Amorpha-4,11-Diene, a Precursor of the Antimalarial Agent Artemisinin, in *Escherichia coli*. PLos One, 2009, vol. 4(2), e4489, pp. 1-12. (Year: 2009).*
George et al., Isoprenoid Drugs, Biofuels, and Chemicals-Artemisinin, Farnesene, and Beyond. Adv Biochem Eng Biotechnol., 2015, vol. 148: 355-389. (Year: 2015).*
Wong et al., Microbial Production of Isoprenoids. Springer International Publishing AG 2016 S.Y. Lee (ed.), Consequences of Microbial Interactions with Hydrocarbons, Oils, and Lipids: Production of Fuels and Chemicals, Handbook of Hydrocarbon and Lipid Microbiology, pp. 1-24. (Year: 2016).*
PCT International Search Report and Written Opinion for International Application No. PCT/GB2018/050223, dated Apr. 26, 2018, 11 pages.
Leferink et al, "A 'Plug and Play' Platform for the Production of Diverse Monoterpene Hydrocarbon Scaffolds in *Escherichia coli*", Chemistryselect, Jun. 2016, vol. 1, No. 9, pp. 1893-1896.
Nakano et al, "Identification and Characterization of the Linalool/Nerolidol Synthase from Streptomyces clavuligerus", Chembiochem—A European Journal of Chemical Biology, Nov. 2011,vol. 12, No. 16, pp. 2403-2407.

(Continued)

*Primary Examiner* — Ganapathirama Raghu
(74) *Attorney, Agent, or Firm* — Hoffman Warnick LLC

(57) ABSTRACT

The present invention relates to a process of producing a monoterpene and/or derivatives thereof. The process comprises the steps of: a) providing a host microorganism genetically engineered to express a bacterial monoterpene synthase (mTS); and b) contacting geranyl pyrophosphate (GPP) with said bacterial mTS to produce said monoterpene and/or derivatives thereof. The present invention also relates to a microorganism for use in producing a monoterpene and/or derivatives thereof and a recombinant microorganism adapted to conduct the step of converting geranyl pyrophosphate (GPP) into a monoterpene and/or derivatives thereof by ex-pression of a bacterial mTS. It was shown to produce 1,8 cineole using 1,8 cineole synthase and to produce linalool using linalool synthase, both from *Streptomyces clavuligerus*.

10 Claims, 4 Drawing Sheets

Figure 1:
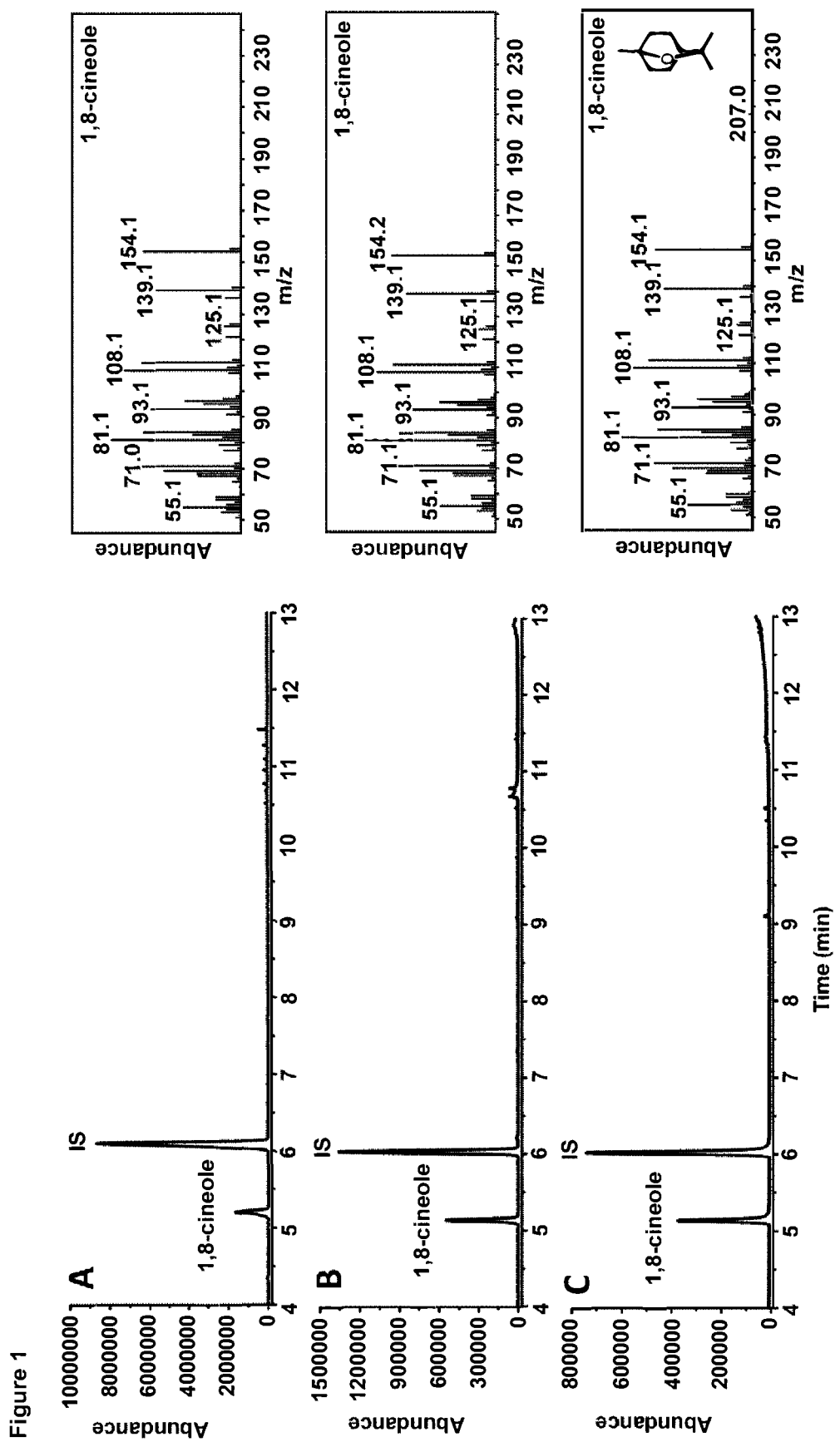
Figure 1:
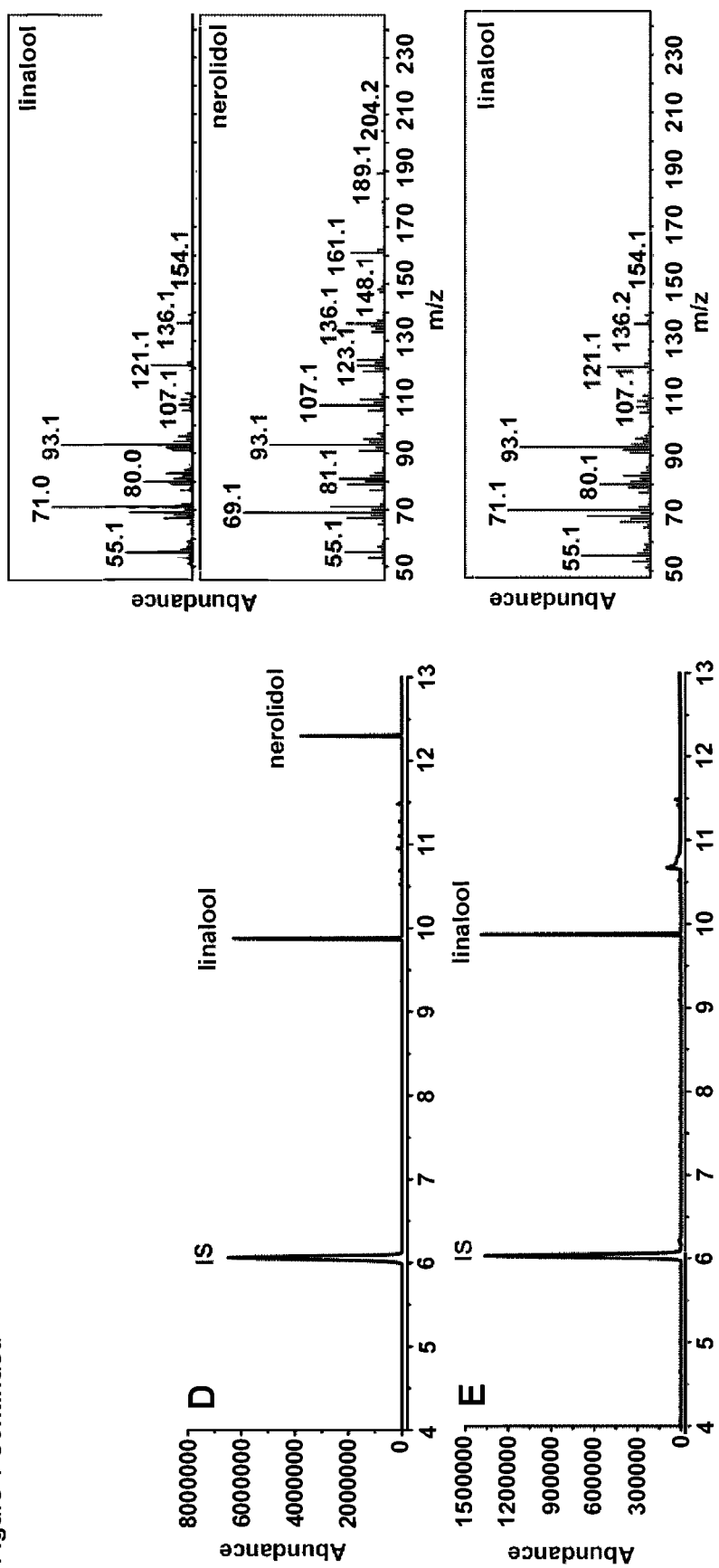
Figure 1:
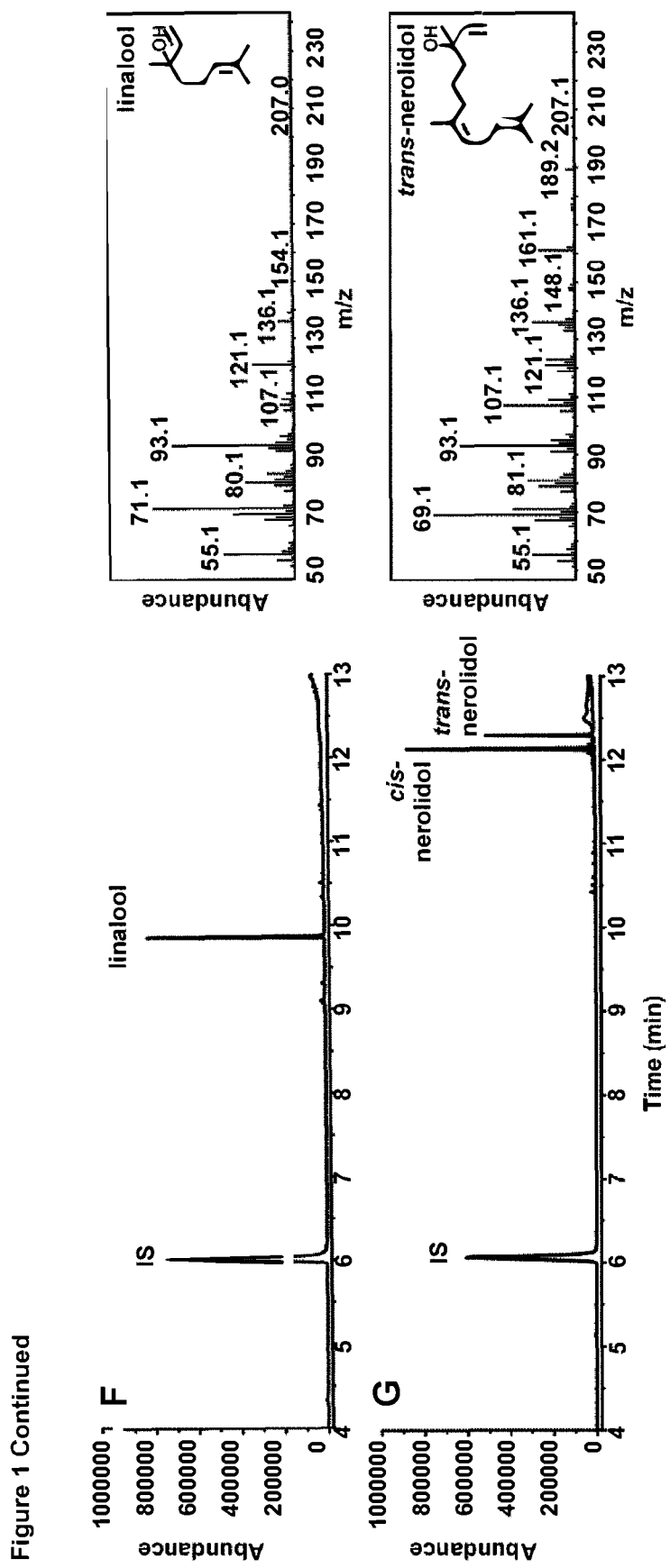

Specification includes a Sequence Listing.

(56) References Cited

OTHER PUBLICATIONS

Nakano et al, "Identification of the First Bacterial Monoterpene Cyclase, a 1,8-Cineole Synthase, that Catalyzes the Direct Conversion of Geranyl Diphosphate", Chembiochem—A European Journal of Chemical Biology, Jul. 2011 vol. 12, No. 13, pp. 1988-1991.
Karuppiah et al, "Structural Basis of Catalysis in the Bacterial Monoterpene Synthases Linalool Synthase and 1,8-Cineole Synthase", ACS Catalysis, Aug. 2017, vol. 7, No. 9, pp. 6268-6282.
Yamada et al, "Terpene synthases are widely distributed in bacteria", Proceedings National Academy of Sciences PNAS, Dec. 2014, vol. 112, No. 3, pp. 857-862.
India Examination Report for Application No. 201917029931, dated Feb. 26, 2021, 6 pages.
Eisenreicha et al., "Biosynthesis of isoprenoids via the non-mevalonate pathway," CMLS Cellular and Molecular Life Sciences, 61, 2004, 1401-1426.
Kuzuyama et al., "Heterologous Mevalonate Production in Streptomyces lividans TK23," Taylor & Francis Group, Bioscience, Biotechnology, and Biochemistry, 68, 4, 2004, 931-934.

\* cited by examiner

SEQUENCE LISTING

<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Primer sequence

<400> SEQUENCE: 1

-continued

```
catccccact actgagaatc                                                20

<210> SEQ ID NO 2
<211> LENGTH: 19
<212> TYPE: DNA
<213> ORGANISM: Artificial Sequence
<220> FEATURE:
<223> OTHER INFORMATION: Primer sequence

<400> SEQUENCE: 2
ggtggtggtg ctcgagtta                                                 19

<210> SEQ ID NO 3
<211> LENGTH: 22
<212> TYPE: DNA
<213> ORGANISM: Artificial Sequence
<220> FEATURE:
<223> OTHER INFORMATION: Primer sequence

<400> SEQUENCE: 3
taactcgagc accaccacca cc                                             22

<210> SEQ ID NO 4
<211> LENGTH: 24
<212> TYPE: DNA
<213> ORGANISM: Artificial Sequence
<220> FEATURE:
<223> OTHER INFORMATION: Primer sequence

<400> SEQUENCE: 4
tcagtagtgg ggatgtcgta atcg                                           24
```

PROCESS OF PRODUCING MONOTERPENES

FIELD OF THE INVENTION

The present invention relates to a process of producing monoterpenes. In particular, the present invention relates to a process of producing monoterpenes, for example in a host microorganism, by the action of a bacterial monoterpene synthase.

BACKGROUND TO THE INVENTION

Terpenoids (also called isoprenoids) are the most abundant and largest class (>75000) of natural products. Most commonly found in plants, their biological roles are multitude ranging from species to species communication to intracellular signalling and defence against predatory species. They have a wide range of applications and are used in pharmaceuticals, herbicides, flavourings, fragrances and biofuels. Due to the broad commercial interest for terpenoids, efforts to synthesize them by synthetic biology routes have gathered pace in recent years.

Terpenoid substrates are synthesized from the C5 isoprene building blocks, namely dimethylallyl pyrophosphate (DMAPP) and isopentenyl pyrophosphate (IPP). Combination of DMAPP and IPP can generate substrates of varying carbon lengths, which can then be utilized by terpene synthases/cyclases to produce monoterpenes (C10), sesquiterpenes (C15), diterpenes (C20) and others. For example, geranyl pyrophosphate (GPP), the substrate for making all monoterpenes is synthesized by coupling one molecule each of DMAPP and IPP.

Monoterpene synthases (mTS) are enzymes that use a single C10 substrate molecule geranyl pyrophosphate (GPP) to produce several thousand diverse monoterpenes. The structure of plant mTS has a two domain architecture: a class I terpenoid fold C-terminal domain and a relatively small N-terminal domain whose function is unclear. The amino acid sequence variations in the active site combined with conserved residues for GPP recognition results in mTS carrying out some of the most complex reactions in biology leading to the formation of linear, monocyclic and bicyclic terpenoids.

Many monoterpene hydrocarbon scaffolds have been produced in engineered microbes in recent years, using yeast or E. coli as a host and employing mTS from plant sources. However, the resulting monoterpene yields are relatively low. Examples of monoterpenoids produced in such systems include geraniol, β-myrcene, limonene and pinene.

E. coli is the workhorse for recombinant protein production around the world in both academia and industry. This preferred choice is due to the ease of introducing external DNA material into the cell, a fast growth cycle and the use of inexpensive growth media. As mentioned above, for the production of monoterpenes using synthetic biology routes, plant mTS have been utilised. However, the use of such plant mTS has associated disadvantages.

Experiments by the inventors have revealed that many plant mTS when overexpressed in E. coli, generate mostly insoluble protein i.e., inactive material not suitable for monoterpene biosynthesis. This limited solubility has proved to be a bottleneck in the production of monoterpenes as the majority of the GPP molecules in the host cell are not utilised for the synthesis of monoterpenes, resulting in low product yields/titres. This is particularly the case for biosynthesis of linalool, which is widely used as perfume in cleaning agents. Plant linalool synthases when employed in either yeast or E. coli result in very low product titres (0.1-1 mg/$L_{org}^{-1}$). The presence of geranoid by-products (>10-fold excess) resulting from endogenous E. coli activity shows that substrate availability is not the cause of these observed low titres. Lack of robustness also makes plant mTS less attractive targets for protein engineering. In addition, mTS enzymes from plant sources often show a high degree of product diversity resulting in product mixtures rather than clean product profiles. This is particularly the case for the more complex bi-cyclic monoterpene scaffolds such as 1,8-cineole (also called eucalyptol), which is used in flavourings, fragrances and cosmetics. Employing cineole synthases from several different plant sources all resulted in relative 1,8-cineole amounts of 42-64% (Leferink, N. G. H. et al. A 'Plug and Play' Platform for the Production of Diverse Monoterpene Hydrocarbon Scaffolds in *Escherichia coli*. (2016)). The generation of single, clean products is desirable, as this would require less downstream processing.

It is an object of the present invention to obviate or mitigate one or more of the abovementioned problems.

SUMMARY OF THE INVENTION

The present invention relates to a process of producing monoterpenes and/or derivatives thereof. The present invention also relates to microorganisms for use in producing a monoterpene and/or derivatives thereof and recombinant microorganisms adapted to produce monoterpenes.

The invention is based in part on studies by the inventors in which they showed that the expression of certain bacterial monoterpene synthases (mTS) in E. coli results in a high yield of high purity monoterpenes.

The process of producing monoterpenes and/or derivatives thereof comprises the steps of providing a host microorganism genetically modified to express a bacterial monoterpene synthase (mTS) and contacting geranyl pyrophosphate with said bacterial mTS to produce said monoterpene and/or derivatives thereof.

In a first aspect of the invention there is provided a process of producing a monoterpene and/or derivatives thereof in a host microorganism. The process comprises the following steps:
  a) providing a host microorganism genetically modified to express a bacterial monoterpene synthase (mTS); and
  b) contacting geranyl pyrophosphate (GPP) with said bacterial mTS to produce said monoterpene and/or derivatives thereof.

In studies undertaken by the present inventors, they have surprisingly shown that it is possible to produce high yields of highly pure monoterpenes in host microorganisms when utilising bacterial monoterpene synthases. As discussed in more detail below, the yield and purity obtained when using bacterial mTS was surprisingly much higher than when plant-derived mTS were utilised.

Monoterpenes and/or Derivatives Thereof

The process of the present invention comprises contacting geranyl pyrophosphate (GPP) with said bacterial mTS to produce said monoterpene and/or derivatives thereof.

As will be appreciated by the skilled person, the term monoterpene and/or derivative thereof is used to define a 'product' monoterpene different to the 'starting material' geranyl pyrophosphate.

As described above, terpenes, for example monoterpenes have a variety of applications including in pharmaceuticals, herbicides, flavourings, fragrances and biofuels. The monoterpene produced in the process of the first aspect of the invention can be any suitable monoterpene or derivative thereof. Suitable derivatives of the monoterpenes of the invention may be obtained by alkylation, oxidation or reduction for example. For example, monoterpene derivatives may include monoterpenoids.

As will be appreciated by the skilled person the monoterpene derivatives may be produced by chemical derivitisation of the monoterpene independent of the mTS.

Alternatively, the monoterpene derivatives may be produced biologically by the mTS itself or another enzyme present in the host microorganism.

The monoterpene or derivative thereof produced in the process of the first aspect of the invention may be geraniol, ocimene, citral, citronellal, citronellol, linalool, halomon, limonene, pinene, carene, sabinene, camphene, thujene, camphor, borneol, terpioline, terpinene, phellandrene, terpineol, fenchol, 1,8-cineole or β-myrcene for example.

In embodiments of the invention, the monoterpene may be linalool or 1,8-cineole and/or derivatives thereof.

Host Microorganism

The host microorganisms of the present invention may be non-naturally occurring microorganisms for example genetically modified bacteria, archaea, yeast, fungus, algae or any of a variety of other microorganisms.

In embodiments of the invention, the host microorganisms are bacteria. Examples of suitable bacteria include enterobacteria belonging to proteobacteria of the genus *Escherichia, Enterobacter, Pantoea, Klebsiella, Serratia, Erwinia, Salmonella* or *Morganella*, coryneform bacteria belonging to the genus *Brevibacterium, Corynebacterium* or *Microbacterium* and bacteria belonging to the genus *Alicyclobacillus, Bacillus, Hydrogenobacter, Methanococcus, Acetobacter, Acinetobacter, Agrobacterium, Axorhizobium, Azotobacter, Anaplasma, Bacteroides, Bartonella, Bordetella, Borrelia, Brucella, Burkholderia, Calymmatobacterium, Campylobacter, Chlamydia, Chlamydophila, Clostridium, Coxiella, Ehrlichia, Enterococcus, Francisella, Fusobacterium, Gardnerella, Haemophilus, Helicobacter, Kelbsiella, Methanobacterium, Micrococcus, Moraxella, Mycobacterium, Mycoplasma, Neisseria, Pasteurella, Peptostreptococcus, Porphyromonas, Prevotella, Pseudomonas, Rhizobium, Rickettsia, Rochalimaea, Rothia, Shigella, Staphylococcus, Stenotrophomonas, Streptococcus, Treponema, Vibrio, Wolbachia* or *Yersinia*.

Preferably the bacteria is of the genus *Escherichia*, preferably *Escherichia coli*.

In embodiments in which the host microorganism is *Escherichia coli* (*E. coli*), the *E. coli* may be of one or more of K-12, B or W strains. For example, the host microorganism may comprise one or more of the following strains: DH5a, DH10p, MG1655, W3110, DHI1, MDS42, BL21 or Mach1.

Examples of suitable yeasts or fungi include those belonging to the genera *Saccharomyces, Schizosaccharomyces, Candida, Kluyveromyces, Aspergillus, Pichia* or *Crytpococcus*. In embodiments, yeast or fungi species include those selected from *Saccharomyces cerevisiae, Schizosaccharomyces pombe, Kluyveromyces lactis, Kluyveromyces marxianus, Aspergillus terreus, Aspergillus niger* or *Pichia pastoris*, for example.

The host microorganism of the first aspect of the invention is genetically modified (for example genetically engineered) to express a bacterial monoterpene synthase (mTS).

As will be appreciated by the skilled person, the host microorganism in which the monoterpene is produced may be the same host microorganism which is genetically engineered to express a bacterial mTS.

The skilled person will appreciate that, in embodiments, the host microorganism may be genetically modified to express a bacterial monoterpene synthase not naturally encoded or expressed in the host microorganism. The skilled person will further appreciate, that in embodiments, the host microorganism may be genetically modified to produce more bacterial monoterpene synthase than a wildtype microorganism which encodes or expresses such a bacterial mTS.

Enhancing the production of bacterial mTS compared to a wildtype microorganism may include making modifications to existing nucleic acids and/or proteins (for example by introducing a strong promoter before a normally silent or poorly expressed gene) by use of various genetic modification techniques known in the art, as discussed further below. Enhancing the production of bacterial mTS compared to a wildtype microorganism may also include modifying the microorganism to express one or more heterologous genes in the microorganism, for example a gene encoding a bacterial mTS from another microorganism, or genes which act to promote the functioning and expression of a bacterial mTS either directly or indirectly. For example, in embodiments, the host microorganism may be *E. coli* which has been genetically modified to express a bacterial mTS from an alternative bacterial species, for example *Streptomyces*.

The host microorganisms of the present invention may be modified to enhance production of monoterpenes and/or derivatives thereof. For example, the microorganisms may comprise modifications which decrease or eliminate the activity of an enzyme that catalyses synthesis of a compound other than monoterpenes by competing for the same substrates and/or intermediates (for example GPP). Alternatively, or in addition, the host microorganisms used in the process of the present invention may comprise modifications that decrease or eliminate the activity of an enzyme which metabolises monoterpenes or intermediates in the production of monoterpenes.

Enhancing the production of monoterpenes may include selecting host microorganisms which are adapted to produce more monoterpene compared to a wildtype microorganism. In the context of the present invention, the term 'adapted' when used in relation to a host microorganism means a genetically modified or engineered organism, or a mutant strain of an organism, which has been selected on the basis that it expresses one or more enzymes which result in enhanced production of monoterpenes.

In order to modify the activity of enzymes or proteins, mutations for increasing, reducing or eliminating intracellular activities of the enzymes or proteins can be introduced into the genes of the enzymes or proteins by conventional random or site directed mutagenesis or genetic engineering techniques. Examples of the mutagenesis can include, for example, X-ray or ultraviolet ray irradiation, treatment with a mutagen, in vitro site directed or random mutagenesis by the polymerase chain reaction. The site on the gene where the mutation is introduced can be in the coding region encoding the enzyme or protein or an expression control region such as a promoter. Examples of genetic engineering techniques include genetic recombination, transduction, cell fusion and gene knockouts.

Nucleic acid sequences can be introduced stably or transiently into a host microorganism using techniques well known to the skilled person, including, for example, conjugation, electroporation, chemical transformation, transduction, transfection and ultrasound transformation.

Methods for constructing and testing the expression of a protein in a modified host microorganism can be performed using recombinant techniques and detection methods well known to the skilled person, for example as described in Sambrook and Russell, Molecular Cloning: A Laboratory Manual, Third Ed., Cold Spring Harbor Laboratory, New York (2001).

An expression vector or vectors can be constructed to include one or more enzymes (for example a bacterial mTS) operably linked to expression control sequences functional in the microorganisms. Expression vectors applicable for use in the microorganisms of the invention include, for example, plasmids, cosmids, phage vectors, viral vectors, episomes and artificial chromosomes, including vectors and selection sequences or markers operable for stable integration into a host chromosome.

Additionally, the expression vectors can include one or more selectable marker genes and appropriate expression control sequences. Selectable marker genes also can be included that, for example, provide resistance to antibiotics or toxins, complement auxotrophic deficiencies, or supply critical nutrients not in the culture media. Expression control sequences can include constitutive, inducible or repressible promoters, transcription enhancers, transcription terminators or translation signals for example.

Enhancement of the activity of an enzyme can include enhancing expression of a target gene (for example a mTS) by replacing an expression regulatory sequence of the target gene such as a promoter on the genomic DNA or plasmid with a promoter which has an appropriate strength. For example, the thr promoter, lac promoter, trp promoter, trc promoter, pL promoter and tac promoter will be well known to the skilled person. Examples of promoters with high expression activity in microorganisms such as bacteria can include promoters of the elongation factor Tu (EF-Tu) gene, tuf, promoters of genes that encode co-chaperonin GroES/EL and thioredoxin reductase, for example. Examples of strong promoters and methods for evaluating the strength of promoters are well known in the art. Moreover, it is also possible to substitute several nucleotides in a promoter region of a gene, so that the promoter has an appropriate strength.

In embodiments, the host microorganism may express (either naturally or by genetic modification) one or more enzymes which can convert isopentanyl diphosphate (IPP) and dimethylallyl diphosphate (DMAPP) into geranyl pyrophosphate (GPP). In embodiments, the one or more enzymes may be a prenyltransferase under EC number 2.5.1.X, for example geranyl-diphosphate synthase under EC number 2.5.1.1. In embodiments, the prenyltransferase may be from *Abies grandis*, for example.

Therefore, in embodiments, the process may further comprise a step of converting IPP and DMAPP into GPP. Conversion may be achieved by the action of a prenyltransferase as described above.

In embodiments, the host microorganism may express (either naturally or by genetic modification) one or more enzymes which can convert acetyl CoA into IPP, for example by way of the mevalonate-dependent (MVA) pathway. In embodiments, the one or more enzymes may include, for example, acetoacetyl-CoA thiolase (AtoB, EC 2.3.1.9) (from *E. coli* for example), hydroxymethylglutaryl-CoA synthase (HMGS, EC 2.3.3.10) (from *S. cerevisiae* for example), hydroxymethylglutaryl-CoA reductase (HMGR, EC 1.1.1.34) (from *S. cerevisiae* for example), mevalonate kinase (MK, EC 2.7.1.36) (from *S. cerevisiae* for example), phosphomevalonate kinase (PMK, EC 2.7.4.2) (from *S. cerevisiae* for example), phosphomevalonate decarboxylase (PMD, EC 4.1.1.33) (from *S. cerevisiae* for example) and/or isopentenyldiphosphate isomerase (idi, EC 5.3.3.2) (from *E. coli* for example).

Therefore, in embodiments, the process may further comprise a step of converting acetyl CoA into IPP. Conversion may be achieved by the action of one or more of the enzymes described above, for example.

Alternatively, or in addition, the host microorganism may express (either naturally or by genetic modification) one or more enzymes which can convert pyruvate into DMAPP, for example by way of the methylerythritol 4-phosphate (MEP) pathway. In embodiments, the one or more enzymes may include, for example, 1-deoxyxylulose-5-phosphate synthase (DXS, EC 2.2.1.7), 1-deoxyxylulose-5-phosphate reductoisomerase (DXR, IspC, EC 1.1.1.267), 2-C-methyl-D-erythritol 4-phosphate cytidylyltransferase (YgbP, IspD, EC 2.7.7.60), 4-(cytidine 5'-diphospho)-2-C-methyl-D-erythritol kinase (YchB, IspE, EC 2.7.1.148), (E)-4-hydroxy-3-methylbut-2-enyl-diphosphate synthase (GcpE, IspG, EC 1.17.7.1) and/or 4-hydroxy-3-methylbut-2-en-1-yl diphosphate reductase (LytB, IspH, EC 1.17.7.4). In embodiments, such enzymes may be from *E. coli*, for example.

Therefore, in embodiments, the process may further comprise a step of converting pyruvate into DMAPP. Conversion may be achieved by the action of one or more of the enzymes described above, for example.

In a further aspect of the invention there is provided a microorganism for use in producing a monoterpene and/or derivatives thereof according to the process of the first aspect of the invention.

There is further provided a recombinant microorganism adapted to conduct the following step:

a) converting geranyl pyrophosphate (GPP) into a monoterpene and/or derivative thereof by expression of a bacterial mTS.

The recombinant microorganism may be in accordance with the host microorganism described in relation to the first aspect of the invention.

In the context of the present invention, the term 'recombinant microorganism' is used to mean a genetically modified or engineered organism comprising genetic material which has been artificially constructed and inserted into the organism. The genetic material may comprise endogenous or heterologous nucleic acids.

The term 'endogenous' means deriving from the same species of organism. The term 'heterologous' means deriving from a different species of organism.

There is yet further provided a microorganism genetically modified to express a bacterial mTS.

The microorganism may be in accordance with the host microorganism described in relation to the first aspect of the invention.

Monoterpene Synthase

The process of the present invention comprises contacting geranyl pyrophosphate (GPP) with a bacterial mTS to produce a monoterpene and/or derivatives thereof. The GPP is converted to the monoterpene and/or derivatives thereof by the action of the bacterial mTS.

As mentioned above, the present inventors have surprisingly demonstrated that particularly high yields and purities of monoterpenes can be obtained when utilising bacterial mTS to convert GPP to monoterpenes.

As will be appreciated by the skilled person, the bacterial mTS of the present invention may be obtained from a bacterial species which is the same as the host microorganism (i.e. the mTS may be endogenous). For example, the host microorganism may comprise *E. coli* and the bacterial mTS may be obtained from (i.e. originate from) *E. coli*.

Alternatively, the bacterial mTS may be obtained from a bacterial species different to the host microorganism (i.e. the mTS may be heterogenous). For example, the host microorganism may be a yeast or the host microorganism may be *E. coli* and the bacterial mTS may be obtained from a different bacterial species, for example *Streptomyces*.

The bacterial mTS may be a bacterial monoterpene synthase under EC number 4.2.3.x.

Sources of nucleic acids for genes encoding the bacterial mTS can include, for example, any species where the encoded gene product is capable of catalysing the conversion of GPP to a monoterpene or derivative thereof. Exemplary bacterial sources include *Escherichia coli, Propionibacterium fredenreichii, Methylobacterium extorquens, Shigella flexneri, Salmonella enterica, Yersinia frederiksenii, Propionibacterium acnes, Bacillus cereus, Acinetobacter calcoaceticus, Acinetobacter baylyi, Acinetobacter* sp., *Clostridium kluyveri, Pseudomonas* sp., *Pseudomonas aeruginosa, Pseudomonas putida, Pseudomonas fluorescens, Thermus thermophilus, Clostridium acetobutylicum, Clostridium cochlearium, Clostridium tetanomorphum, Clostridium tetani, Clostridium pasteurianum, Clostridium propionicum, Clostridium saccharoperbutylacetonicum Leuconostoc mesenteroides, Eubacterium barkeri, Bacteroides capillosus, Anaerotruncus colihominis, Natranaerobius thermophilus, Campylobacter jejuni, Corynebacterium glutamicum, Bacillus subtilus, Serratia marcescens, Streptomyces* species for example *Streptomyces coelicolor, Streptomyces cinnamonensis, Streptomyces avermitilis* or *Streptomyces clavuligerus*, or *Helicobacter* pylon.

In preferred embodiments of the present invention, the bacterial mTS is derived from a *Streptomyces* species, for example *Streptomyces clavuligerus*. The present inventors have surprisingly shown that mTS derived from *Streptomyces* are particularly efficient at producing monoterpenes with high purity and at high yield. In embodiments, the bacterial mTS is derived from *Streptomyces clavuligerus*.

In embodiments of the present invention, the bacterial mTS may comprise 1,8-cineole synthase under EC number 4.2.3.108 and/or linalool synthase under EC number 4.2.3.25 or 4.2.3.26. As will be appreciated, in such embodiments, the monoterpene produced comprises 1,8-cineole or linalool respectively.

In embodiments of the present invention, the bacterial mTS may comprise 1,8-cineole synthase and/or linalool synthase derived from *Streptomyces clavuligerus*.

The bacterial mTS when utilised in the process of the first aspect of the present invention preferably produces a monoterpene yield (or titre) of at least 100 mg/$L_{org}^{-1}$.

More preferably, the bacterial mTS produces a monoterpene yield of at least 150, 200, 250 or 300 mg/$L_{org}^{-1}$. Most preferably, the bacterial mTS produces a monoterpene yield of at least 350 mg/$L_{org}^{-1}$. The yield of monoterpene may be measured as described in Leferink et al, 2016, for example by GC or GCMS and quantified during authentic standards. Yields are given as the amount of product per litre of organic phase in which the products are captured.

As such, there is also provided the use of a bacterial mTS to improve the yield (or titre) of a monoterpene and/or derivative thereof obtained from GPP. In embodiments, the monoterpene is obtained from GPP in a host microorganism. Suitably, the yield is improved compared to the yield of a monoterpene and/or derivative thereof obtained from GPP using a plant mTS.

As will be appreciated, the bacterial mTS and host microorganism may be in accordance with those described in relation to the first aspect of the invention.

The bacterial mTS utilised in the process of the first aspect of the invention preferably produces a monoterpene which is at least around 70% pure. When referring to purity, we refer to the amount of monoterpene produced from GPP, without the formation of by-products, for example other terpenes produced as mixed products (as described in Leferink et al, 2016).

Purities may be determined based on the monoterpenoids produced by the mTS from GPP (as described in Leferink et al, 2016). For example, when bacterial 1,8-cineole synthase is utilised as the mTS, small amounts of α-terpineol and limonene may be produced in addition to the main product, 1,8-cineole. In preferred embodiments, the bacterial mTS utilised produces a monoterpene which is at least around 75, 80, 85 or 90% pure. More preferably the monoterpene produced is at least around 95, 96, 97, 98 or 99% pure.

As such, there is also provided the use of a bacterial mTS to improve the purity of a monoterpene and/or derivative thereof obtained from GPP. In embodiments, the monoterpene is obtained from GPP in a host microorganism. Suitably, the purity is improved compared to the purity of a monoterpene and/or derivative thereof obtained from GPP using a plant mTS.

As will be appreciated, the bacterial mTS and host microorganism may be in accordance with those described in relation to the first aspect of the invention.

In embodiments of the invention, the bacterial mTS does not comprise a N-terminal α-barrel domain. Many plant mTS comprise N-terminal α-barrel domains. However, as described above, plant mTS when overexpressed in *E. coli*, generate mostly insoluble protein. Without wishing to be bound by theory, the present inventors hypothesise that the additional domain present in many plant mTS may contribute to the insolubility of the mTS in the host microorganism. It may therefore be beneficial to utilise a bacterial mTS which does not comprise a N-terminal α-barrel domain.

Further Process Steps

In the first aspect of the present invention, monoterpenes and/or derivatives thereof may be produced by the host microorganisms in a fermentation medium. The host microorganisms of the present invention may be provided in a fermentation medium under conditions which said host microorganism will produce a monoterpene or derivative thereof.

In embodiments, the process of the first aspect of the invention comprises culturing the host microorganism in said fermentation medium. Culturing may require a carbon based feedstock from which the microorganism may derive energy and grow.

The fermentation medium may be a surrounding medium which surrounds the host microorganism. Preferably a carbon based feedstock is present in the medium, for example dissolved or suspended in the medium or mixed with the medium.

The fermentation medium may be any commercially available medium suitable for the needs of the host microorganism as will be well known to the skilled person. The fermentation medium may comprise a carbon based feedstock and a nitrogen source, as well as additional compounds required for growth of the host microorganism, for example, antibiotics, buffers, phosphate, sulphate, magnesium salts etc.

Suitable carbon based feedstocks will be well known to the skilled person working in this field of technology. The carbon based feedstock may include, for example, glucose, maltose, sucrose, starch and/or may be derived from wastes, for example food waste or wastes from industry, such as forestry or agriculture.

The amount of feedstock required will vary depending on the needs of the host microorganism and the length of culturing of the host microorganism, for example.

As will be appreciated by the skilled person, the host microorganism may be genetically modified to produce GPP (as set out above) or the GPP may be provided in the fermentation medium, for example.

The host microorganism may be cultured as a batch, fed-batch or continuous process. Preferably, the culturing is performed on an industrial scale.

In embodiments, the process of the present invention may further comprise the step of removing the monoterpene and/or derivative thereof from the host microorganism, for example extracting the monoterpene from the host microorganism or fermentation medium in which the host microorganism is cultured. For example, when the host microorganism is present in a fermentation medium, the process may comprise removing or extracting the monoterpene or derivative thereof from contact with the fermentation medium.

In embodiments, removing the monoterpene and/or derivative thereof may comprise solvent extraction. For example, an organic phase may be provided in contact with the fermentation medium. The organic phase may include the monoterpene in a higher concentration than that in the fermentation medium. The organic phase may be an organic solvent, for example. As will be appreciated by the skilled person, any suitable organic solvent could be utilised, and may comprise nonane (for example n-nonane), dodecane (for example n-dodecane), hexadecane (for example n-hexadecane) or diisononyl phthalate.

Alternatively, the monoterpene may be removed from the fermentation medium by steam distillation, under supercritical carbon dioxide or by pressurisation, for example.

The described and illustrated embodiments are to be considered as illustrative and not restrictive in character, it being understood that only the preferred embodiments have been shown and described and that all changes and modifications that come within the scope of the inventions as defined in the claims are desired to be protected.

Moreover, any one or more of the above described preferred embodiments could be combined with one or more of the other preferred embodiments to suit a particular application.

It should be understood that while the use of words such as "preferable", "preferably", "preferred" or "more preferred" in the description suggest that a feature so described may be desirable, it may nevertheless not be necessary and embodiments lacking such a feature may be contemplated as within the scope of the invention as defined in the appended claims. In relation to the claims, it is intended that when words such as "a," "an," or "at least one," are used to preface a feature there is no intention to limit the claim to only one such feature unless specifically stated to the contrary in the claim.

DETAILED DESCRIPTION OF THE INVENTION

The present invention will now be further described with reference to the following figures which show:

FIG. 1: GC-MS analysis using bacterial 1,8-cineole synthase (bCinS) and bacterial linalool synthase (bLinS). A) bCinS platform product profile. B) bCinS conversion of GPP (20 mM). C) 1,8-cineole standard (0.1 mg/ml). D) bLinS platform product profile. E) bLinS conversion of GPP (20 mM). F) R-linalool standard (0.1 mg/ml). G) cis- and trans-nerolidol standards (0.1 mg/ml). IS=internal standard (sec-butyl benzene).

Figure 2:
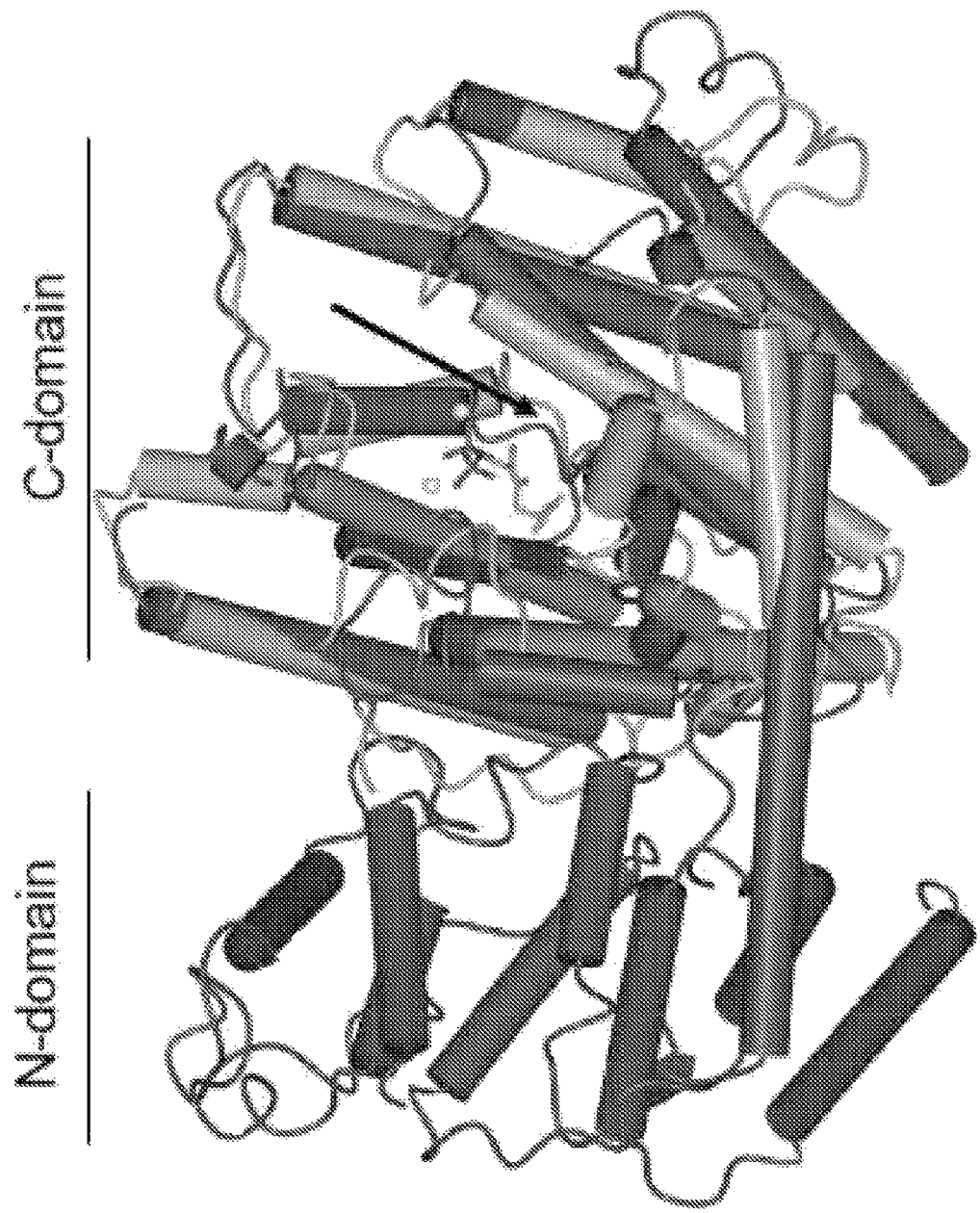

FIG. 2: Structure of bCinS-FNPP complex. Superposition of plant cineole synthase (dark) and bCinS (light). The N-terminal and C-terminal domains of the plant CinS are labelled. An arrow indicates the conformational difference in the helix-break motif.

MATERIALS AND METHODS

Expression and purification of bacterial 1,8-cineole synthase (bCinS) and bacterial linalool synthase (bLinS) The full-length genes coding for 1,8-cineole synthase (WP_003952918) and linalool synthase (WP_0003957954) from *Streptomyces clavuligerus* ATCC 27064 were codon optimized and synthesized from GeneArt (Life Technologies). The genes were amplified using PCR and sub-cloned into double digested (NcoI and XhoI) pETM11 vector using Infusion cloning (Clontech). The final construct coded for either 1,8-cineole synthase (bCinS) or linalool synthase (bLinS) with a 6X-His tag followed by a TEV protease cleavage site at the N-terminus. The expression and purification method explained below was identical for both the proteins.

The plasmid was transformed into ArcticExpress (DE3) cells (Agilent) and few colonies were inoculated into 100 ml 2X-YT media containing 40 μg/ml of kanamycin and 20 μg/ml of gentamycin and grown for 3-4 hours at 37° C. The culture was diluted into 3 l of fresh 2X-YT media containing 40 μg/ml of kanamycin and allowed to grow at 37° C. until the OD at 600 nm reached 0.6-0.8. At this stage, the temperature was reduced to 16° C. and 0.1 mM Isopropyl β-D-1-thiogalactopyranoside was added and incubated for 14-18 hours. The cells were harvested by centrifugation at 6000 g for 10 minutes and the pellet was resuspended in buffer A (25 mM Tris pH 8.0, 150 mM NaCl, 1 mM DTT, 4 mM $MgCl_2$ and 5%(v/v) glycerol). The cells were lysed by sonication and the debris was removed by centrifugation at 30,000 g for 30 minutes. The supernatant was filtered through a 0.2 μm filter and loaded onto a 5 ml HisTrap column (GE Healthcare) pre-equilibrated with buffer A. The column was washed with buffer A containing 10 mM imidazole (pH 8.0) and increasing up to 40 mM imidazole by step gradients with 3 column volume for each concentration. Increasing the concentration of imidazole to 200-500 mM eluted the protein. The purified protein was desalted using Centripure P100 column (emp biotech) equilibrated with buffer A. To remove the His tag, TEV protease was added (1:1000 (w/w)) to the protein and incubated at 4° C. with gentle mixing for 24 hours. The TEV protease was removed by passing the protein mixture through a 5 ml HisTrap column and the flow through was collected. The His-tag removed protein was concentrated and loaded onto a Hiload Superdex (26/60) S75 column (GE Healthcare) pre-equilibrated with buffer A. Pure fractions from the gel filtration column were concentrated to 13-15 mg/ml and stored at −80° C. as aliquots.

Biotransformations

The 0.25 ml reactions were prepared using buffer A and setup in glass vials containing 2 mM GPP and 20 μM of bCinS or bLinS. The vials were incubated at 25° C. with gentle shaking for 16 hours. The vials were cooled down to 4° C. and 0.25 ml of ethyl acetate containing 0.01% sec-butyl benzene as internal standard was added. The samples were vortexed for 2 min and then spun at 18,000 g for 5 min. The supernatant fractions containing the ethyl acetate layer were carefully removed and dried over anhydrous magnesium sulfate. The samples were analysed by GC-MS.

Linalool and 1,8-Cineole Production in *E. coli*

Both bLinS and bCinS genes, including RBS, were amplified from their respective pETM-11 expression vectors using primers pET_IF_Fw (5'-CATCCCCACTACTGAGAATC-3') (SEQ ID No: 1) and pET_IF_Rv (5'-GGTGGTGGTGCTCGAGTTA-3') (SEQ ID No: 2) and cloned using InFusion (Takara) into plasmid pGPPSmTS15, which was PCR linearised using the primer pair Vector_IF_Fw (5'-TAACTCGAGCACCACCACCACC-3') (SEQ ID No: 3) and Vector_IF_Rv (5'-TCAGTAGTGGG-GATGTCGTAATCG-3') (SEQ ID No: 4) resulting in plasmids pGPPSmTS38 and pGPPSmTSS39, respectively. Correct insertion was confirmed by automated sequencing (Eurofins).

For monoterpenoid production the pGPPSmTS plasmids were co-transformed with pMVA into *E. coli* DH5a and grown as described previously (Leferink, N. G. H. et al. A 'Plug and Play' Platform for the Production of Diverse Monoterpene Hydrocarbon Scaffolds in *Escherichia coli*. (2016)). Briefly, expression strains were inoculated in terrific broth (TB) supplemented with 0.4% glucose in glass screw capped vials, and induced for 72 h at 30° C. with 50 µM (isopropyl β-D-1-thiogalactopyranoside) IPTG and 25 nM anhydro-tetracycline (aTet). A 20% n-nonane layer was added to capture the volatile terpenoids products. After induction, the nonane overlay was collected, dried over anhydrous $MgSO_4$ and mixed at a 1:1 ratio with ethyl acetate containing 0.1% (v/v) sec-butyl benzene as internal standard.

GC-MS Analysis

The samples were injected onto an Agilent Technologies 7890B GC equipped with an Agilent Technologies 5977A MSD. The products were separated on a DB-WAX column (30 m×0.32 mm i.d., 0.25 µM film thickness, Agilent Technologies). The injector temperature was set at 240° C. with a split ratio of 20:1 (1 µl injection). The carrier gas was helium with a flow rate of 1 ml min-1 and a pressure of 5.1 psi. The following oven program was used: 50° C. (1 min hold), ramp to 68° C. at 5° C. $min^{-1}$ (2 min hold), and ramp to 230° C. at 25° C. $min^{-1}$ (2 min hold). The ion source temperature of the mass spectrometer (MS) was set to 230° C. and spectra were recorded from m/z 50 to m/z 250. Compound identification was carried out using authentic standards and comparison to reference spectra in the NIST library of MS spectra and fragmentation patterns as described previously (Leferink, N. G. H. et al. A 'Plug and Play' Platform for the Production of Diverse Monoterpene Hydrocarbon Scaffolds in *Escherichia coli*. (2016)).

Chemical Synthesis of FGPP and FNPP

A Horner-Wadsworth-Emmons reaction was performed by treating ethyl (diethoxyphosphoryl)fluoroacetate with sodium hydride followed by 6-methyl-5-hepten-2-one resulting in a mixture of 2-fluoronerol and 2-fluorogeranoil in almost equal ratio (1:1.08) with an 86% yield. The isolated products were then treated with $H_3PO_4(Et_3N)_2$ salt to give the corresponding mono and dephosphorylated products.

Crystallization of bCinS and bLinS

The crystallization trials containing 200 nl of protein and 200 nl of precipitant solution were setup in 3-well swissci plates using mosquito robot (TTP Labtech). Five screens—Morpheus I and II, JCSG+, PACT premier and SG1 (Molecular Dimensions Ltd) were used for initial trails. For bCinS and bLinS, three variants were screened—Apo, with 2 mM FGPP and with 2 mM FNPP. The bCinS-FNPP crystallized in Morpheus II A4 condition (90 mM of LiNaK (0.3 M Lithium sulphate, 0.3 M Sodium sulphate, 0.3 M Potassium sulphate), 0.1 M of buffer system 4 (1 M MOPSO, 1 M Bis-Tris) pH 6.5, and 50% precipitant mix 8 (10% PEG 20000, 50% Trimethyl propane, 2% NDSB 195)). The bLinS-FNPP crystallized in Morpheus D7 condition (0.12 M Alcohols (0.2 M 1,6-Hexanediol; 0.2 M 1-Butanol; 0.2 M 1,2-Propanediol; 0.2 M 2-Propanol; 0.2 M 1,4-Butanediol; 0.2 M 1,3-Propanediol) 0.1 M Buffer System 2 7.5 (1.0 M Sodium HEPES; MOPS (acid)) 50% v/v Precipitant Mix 3 (40% v/v Glycerol; 20% w/v PEG 4000)). LinS-apo crystallized in SG1 E2 condition (25% w/v PEG3350). Although bCinS-apo crystallized, optimization of growth conditions failed to produce single crystals of sufficient size for harvesting. The bCinS-FNPP and bLinS-FGPP crystals were cryo-protected by soaking in mother liquor. The bLinS-apo crystals were cryo-protected by soaking in mother liquor supplemented with 20% glycerol. For FGPP and FNPP complexes, the ligands were included in the cryo-solution. The crystals were harvested and cryo-cooled by plunging in liquid nitrogen.

Structure Solutions

The bLinS and bCinS X-ray datasets were collected at Diamond Light Source (DLS). The images were integrated and scaled by xia2 automated data processing pipeline, using XDS and XSCALE. Crystals of bCinS belonged to the triclinic system (spacegroup P1) and contained two molecules in the asymmetrical unit (ASU), whereas bLinS crystals belonged to the tetragonal system (spacegroup 14) and also contained two molecules in ASU. The bLinS structures (bLinS-apo and bLinS-FGPP) were solved by molecular replacement using Pentalenene synthase structure (PDB 1 PS1) as the search model in Phaser. The bCinS-FNPP structure was solved by model replacement using the bLinS-apo structure as the search model. The bLinS-apo, bLinS-FGPP and bCinS—F-NPP models were built using Autobuild in Phenix. The structures were completed using iterative rounds of manual model building in coot and refinement in phenix.refine. The structures were validated using molprobity tools and PDB_REDO.

Plasmids

Table 1 below shows the plasmids used in this study.

TABLE 1

Plasmids used in this study

| Plasmid reference | Plasmid name | Description (Origin of replication, Antibiotic marker, Reference(s), Promoters and Operons) | Source |
|---|---|---|---|
| pMVA | BbA5a-MTSAe-T1f-MBI(f)-T1002i | p15A, Kanr, PlacUV5, MTSA, T1, MBI-f, T1002 | Leferink et al, 2016 |
| pGPPSmTS15 | pBbB2a-trAgGPPS(co)-trSLimS_Ms | pBBR, Ampr, Ptet, trAgGPPS(co)-trSLimS_Ms | Leferink et al, 2016 |
| pGPPSmTS38 | pBbB2a-trAgGPPS(co)-bLinS | pBBR, Ampr, Ptet, trAgGPPS(co)-bLinS | This study |
| pGPPSmTS39 | pBbB2a-trAgGPPS(co)-bCinS | pBBR, Ampr, Ptet, trAgGPPS(co)-bCinS | This study |

Results

The present inventors undertook significant testing to determine how monoterpenes might be produced in bacterial hosts with greater efficiency. In particular, the experiments undertaken by the inventors surprisingly identified a number of bacterial mTS, including bLinS and bCinS from *Streptomyces clavuligerus*, whose expression in an *E. coli* system resulted in much higher monoterpene production, and in greater purity, than when plant mTS were utilised.

Linalool and 1,8-Cineole Production in *E. coli*

When expressed in *E. coli*, large quantities (>100 mg/litre) of bLinS and bCinS were produced and the enzymes were stable and soluble, when compared to plant mTS which mostly resulted in insoluble or partially soluble material. Biotransformation reactions showed bLinS and bCinS produced linalool and 1,8-cineole respectively when supplied with GPP. No by-products were observed when analyzed by GC-MS (FIG. 1).

To test for suitability in synthetic biology approaches, both bLinS and bCinS were inserted in an *E. coli* 'plug-and-play' monoterpenoid production platform, devised by the inventors, which consists of two gene modules (Leferink, N. G. H. et al. A 'Plug and Play' Platform for the Production of Diverse Monoterpene Hydrocarbon Scaffolds in *Escherichia coli*. (2016)). The first module (pMVA) contains a hybrid MVA pathway under regulation of IPTG-inducible promoters and the second (plasmid series pGPPSmTS, table 1) consists of a refactored, N-terminally truncated geranyl diphosphate synthase (GPPS) gene from *Abies grandis* (AgtrGPPS2) followed by an mTS gene (for example bLinS or bCinS) under control of a tetracycline-inducible promoter.

Strains containing both pMVA and a pGPPSmTS plasmid were grown in a two-phase shake flask system using glucose as the feedstock and n-nonane as the organic phase. Products, which accumulated in the organic phase, were identified and quantified by GC-MS analysis.

Product profiles and titres obtained with bLinS and bCinS were compared with previously obtained product profiles using mTSs from plant sources (FIG. 1), i.e. LinS from *Artemisia annua* (RLinS_Aa) and CinS from *Salvia fruticosa* (CinS_Sf), *Arabidopsis thaliana* (CinS_At), and *Citrus unshiu* (CinS_Cu) (Leferink, N. G. H. et al. A 'Plug and Play' Platform for the Production of Diverse Monoterpene Hydrocarbon Scaffolds in *Escherichia coli*. (2016)).

The inventors surprisingly found that both bacterial mTS outperformed the plant enzymes. BLinS produced about 300-fold more linalool than RLinS_Aa, 363.3±57.9 mg vs 1.3 mg $L_{org}^{-1}$. Without wishing to be bound by theory, it is thought that this high yield can be attributed to the high solubility of BLinS, compared to corresponding plant mTS.

Both bCinS and bLinS also produced much purer monoterpenes that plant mTS. bCinS produced 116.8±36.4 mg $L_{org}^{-1}$ (96% pure) 1,8-cineole compared to the plant enzymes: 118.2 mg $L_{org}^{-1}$ (67% pure) for CinS_Sf; 46.6 mg $L_{org}^{-1}$ (42% pure) for CinS_At; and 18.2 mg $L_{org}^{-1}$ (63% pure) for CinS_Cu.

In addition to the formation of GPP via the heterologous GPPS, *E. coli* natively produces the sesquiterpene precursor farnesyl diphosphate (FPP). Interestingly, plugged into the inventors platform, bLinS was able to convert FPP to nerolidol (159.1±7.3 mg $L_{org}^{-1}$), in addition to the formation of linalool from GPP, suggesting that bLinS acts as both monoterpene and sesquiterpene synthase. No sesquiterpene products were detected for bCinS under the specified conditions when plugged into the platform.

Structure of bCinS Substrate Analog Complex and Comparison with Plant Cineole Synthase The inventors solved the bCinS structure in complex with a 2-fluoro derivative of GPP isomer (FNPP). The FNPP acts as a substrate inhibitor by blocking the ionisation step, which in turn stops the diphosphate release and formation of the geranyl cation. The structure revealed a dimer with the active sites located in an anti-parallel fashion.

The present inventors then compared the structure of bCinS to the structure of 1,8-cineole synthase from a plant in a ligand free state (PDB 2J5C). Compared to the plant enzyme, the bacterial enzyme lacks an N-terminal α-barrel domain (FIG. 2). Comparing the C-terminal domain of the plant enzyme (apo form) with bCinS-FNPP complex (sequence similarly 25%) shows conformational changes around the active site. In the plant enzyme, the kink region of helix break motif of helix G, which encompasses the residues described for induced-fit mechanism, is observed to have the most movement where it is protruding inwards towards the active site and almost reaching the location of the diphosphate in bCinS-FNPP complex (FIG. 2).

It will be appreciated that numerous modifications to the above described process, microorganisms and use thereof may be made without departing from the scope of the invention as defined in the appended claims. For example although the specific examples described have focussed on the monoterpene synthases bCinS and bLinS from *Streptomyces clavuligerus*, it will be appreciated that other monoterpene synthases from alternative bacterial species could be utilised.

SEQUENCE LISTING

SEQ ID No. 1:
catccccact actgagaatc 20
SEQ ID No. 2:
ggtggtggtg ctcgagtta 19
SEQ ID No. 3:
taactcgagc accaccacca cc 22
SEQ ID No. 4:
tcagtagtgg ggatgtcgta atcg 24

---

The invention claimed is:

1. A process of producing linalool in a host microorganism comprising the following steps:
    (a) providing a host microorganism genetically modified to express a bacterial monoterpene synthase (mTS), an *Abies grandis* geranyl diphosphate synthase, and a recombinant mevalonate-dependent (MVA) pathway comprising an *E. coli* acetoacetyl-CoA thiolase (AtoB), an *S. aureus* hydroxymethylglutaryl-CoA synthase (HMGS), an *S. aureus* hydroxymethylglutaryl-CoA reductase (HMGR), an *S. cerevisiae* mevalonate kinase (MK), an *S. Cerevisiae* phosphomevalonate kinase (PMK), an *S. cerevisiae* phosphomevalonate decarboxylase (PMD) and an *E. coli* isopentenyldiphosphate isomerase (idi);
    (b) converting acetyl CoA into isopentenyl diphosphate (IPP) through the recombinant MVA pathway;
    (c) converting IPP and dimethylallyl diphosphate (DMAPP) into geranyl pyrophosphate (GPP) through catalysis by the geranyl diphosphate synthase; and
    (d) contacting GPP with said bacterial mTS to produce linalool,
    wherein the bacterial mTS comprises *Streptomyces clavuligerus* linalool synthase,
    wherein the host microorganism is a genetically modified bacterium comprising *E. coli*, and
    wherein the process results in a linalool yield of at least 300 mg $L_{org}^{-1}$.

2. The process according to claim 1 wherein at least one of the acetoacetyl-CoA thiolase, hydroxymethylglutaryl-CoA synthase, hydroxymethylglutaryl-CoA reductase, mevalonate kinase, phosphomevalonate kinase, phosphomevalonate decarboxylase, isopentenyldiphosphate isomerase, linalool synthase or geranyl diphosphate synthase is modified to enhance the production of linalool.

3. A recombinant microorganism genetically modified to conduct the following step:
    converting geranyl pyrophosphate (GPP) into linalool by expression of a bacterial linalool synthase,
    wherein the microorganism is a genetically modified bacterium comprising *E. coli* and is genetically modified to express *Streptomyces clavuligerus* linalool synthase, an *Abies grandis* geranyl diphosphate synthase, and a recombinant mevalonate-dependent (MVA) pathway comprising an *E. coli* acetoacetyl-CoA thiolase (AtoB), an *S. aureus* hydroxymethylglutaryl-CoA synthase (HMGS), an *S. aureus* hydroxymethylglutaryl-CoA reductase (HMGR), an *S. cerevisiae* mevalonate kinase (MK), an *S. cerevisiae* phosphomevalonate kinase (PMK), an *S. cerevisiae* phosphomevalonate decarboxylase (PMD) and an *E. coli* isopentenyl-diphosphate isomerase (idi).

4. The process according to claim 1, further comprising converting pyruvate into DMAPP, wherein the host microorganism expresses one or more enzymes of the methylerythritol 4-phosphate (MEP) pathway.

5. The process according to claim 4, wherein the host microorganism expresses the following enzymes of the MEP pathway: 1-deoxyxylulose-5-phosphate synthase, 1-deoxyxylulose-5-phosphate reductoisomerase, 2-C-methyl-D-erythritol 4-phosphate cytidylyltransferase, 4-(cytidine 5'-diphospho)-2-C-methyl-D-erythritol kinase, (E)-4-hydroxy-3-methylbut-2-enyl-diphosphate synthase and 4-hydroxy-3-methylbut-2-en-1-yl diphosphate reductase.

6. The process according to claim 5, wherein the enzymes of the MEP pathway are *E. coli* enzymes.

7. The recombinant microorganism according to claim 3, wherein at least one of the acetoacetyl-CoA thiolase, hydroxymethylglutal-CoA synthase, hydroxymethylglutaryl-CoA reductase, mevalonate kinase, phosphomevalonate kinase, phosphomevalonate decarboxylase, isopentenyldiphosphate isomerase, linalool synthase or geranyl diphosphate synthase is modified to enhance the production of linalool.

8. The recombinant microorganism according to claim 3, wherein the microorganism expresses one or more enzymes of the methylerythritol 4-phosphate (MEP) pathway.

9. The recombinant microorganism according to claim 8, wherein the microorganism expresses the following enzymes of the MEP pathway: 1-deoxyxylulose-5-phosphate synthase, 1-deoxyxylulose-5-phosphate reductoisomerase, 2-C-methyl-D-erythritol 4-phosphate cytidylyltransferase, 4-(cytidine 5'-diphospho)-2-C-methyl-D-erythritol kinase, (E)-4-hydroxy-3-methylbut-2-enyl-diphosphate synthase, and 4-hydroxy-3-methylbut-2-en-1-yl diphosphate reductase.

10. The recombinant microorganism according to claim 9, wherein the enzymes of the MEP pathway are *E. coli* enzymes.

* * * * *